United States Patent [19]
Montgomery et al.

[11] Patent Number: 4,717,662
[45] Date of Patent: Jan. 5, 1988

[54] THERMAL STABILIZATION OF ALPHA-AMYLASE

[75] Inventors: Curtis J. Montgomery; Jayarama K. Shetty, both of Elkhart, Ind.; Eric C. Singley, Edwardsburg, Mich.

[73] Assignee: Miles Laboratories, Inc., Elkhart, Ind.

[21] Appl. No.: 768,370

[22] Filed: Aug. 22, 1985

Related U.S. Application Data

[63] Continuation-in-part of Ser. No. 697,036, Jan. 31, 1985, abandoned.

[51] Int. Cl.$^4$ .................. C12P 19/14; C12N 9/96; C12N 9/28; C12R 1/10
[52] U.S. Cl. .................................. 435/99; 435/188; 435/202; 435/836
[58] Field of Search .................. 435/188, 99, 202

[56] References Cited

U.S. PATENT DOCUMENTS

| 905,029 | 7/1908 | Wallerstein . | |
|---|---|---|---|
| 3,524,798 | 8/1970 | Lloyd et al. | 435/202 |
| 3,654,081 | 4/1972 | Vance et al. | 195/31 |
| 3,912,590 | 10/1975 | Slott et al. | 195/31 |
| 4,284,722 | 8/1985 | Tamuri et al. | 435/94 |
| 4,318,818 | 3/1982 | Letton et al. | 252/174.12 |
| 4,497,897 | 2/1985 | Eilertsen et al. | 435/188 |
| 4,642,288 | 2/1987 | Elia De Miguel et al. | 435/99 |

OTHER PUBLICATIONS

Pace et al.; *Journal of Biological Chemistry*; vol. 255, No. 9, May 10, 1980, pp. 3862–3865.

*Primary Examiner*—Lionel M. Shapiro
*Attorney, Agent, or Firm*—Jerome L. Jeffers

[57] ABSTRACT

Disclosed is a method for enhancing the thermal stability of microbial alpha-amylase. The method involves adding a stabilizing amount of an amphiphile to the enzyme in its aqueous solution. Also included within the scope of the invention is the stabilized alpha-amylase formulation and its use in the liquefaction of starch.

21 Claims, 2 Drawing Figures

FIG. 1

FIG. 2

THERMAL STABILIZATION OF ALPHA-AMYLASE

This application is a continuation-in-part of U.S. application Ser. No. 697,036 filed Jan. 31, 1985, now abandoned.

BACKGROUND OF THE INVENTION

The use of thermostable alpha-amylase as a thinning agent during liquefaction of starch represents a significant improvement in the production of sugar sweeteners. The enzymatic liquefaction of starch substrates reduces the formation of undesirable by-products and also permits the use of a low level of salt which is desirable because a high level of salt in the final glucose syrup involves an additional manufacturing cost for its removal by ion exchange resins. The usefulness of an enzyme such as alpha-amylase for liquefying starch at elevated temperatures depends mainly on the enzyme's thermal stability because exposure to heat causes its irreversible denaturation. This denaturation results in the complete loss of biocatalytic activity. Heat stable alpha-amylases obtained from thermophilic microorganisms have been used to hydrolyze, liquefy and/or convert starch containing materials into starch hydrolyzates. For example, U.S. Pat. Nos. 3,654,081 and 3,912,590 describe the liquefaction of starch at high temperatures using thermostable alpha-amylase produced by bacteria of the species *Bacillus licheniformis*.

Many of the commercially available alpha-amylase products are obtained from bacterial sources such as *Bacillus subtilis, B. licheniformis, B. stearothermophilus, B. coagulans*. Fungal alpha-amylases have a very limited application in the liquefaction of starch at high temperatures because they are not generally regarded as thermostable enzymes.

The enzymatic liquefaction of starch is normally carried out at elevated temperatures to increase the susceptibility of the starch to enzymatic hydrolysis. The aforementioned loss of biocatalytic activity can result even with the use of thermostable alpha-amylase at the elevated temperatures preferred for the liquefaction step. Accordingly, stabilizers are added to the enzyme to increase its thermal stability. Thus, it was disclosed by Wallerstein in U.S. Pat. No. 905,029 that the high temperature saccharification of starch by enzymatic means is enhanced by the addition of calcium sulfate to the starch containing medium. The use of calcium ion to thermally stabilize alpha-amylase has become generally accepted in the art but does have certain disadvantages such as the aforementioned problems related to the addition of salts to the starch.

More recently it has been disclosed in U.S. Pat. No. 3,654,081 that starch can be easily and completely liquefied by the addition of calcium and/or sodium salts to an aqueous starch slurry which preferably contains some alpha-amylase.

There is disclosed in U.S. Pat. No. 3,912,590 a process for the combined liquefaction and thinning of starch which involves treating an aqueous starch suspension with alpha-amylase obtained from a bacterium of the species *Bacillus licheniformis* at an elevated temperature.

U.S. Pat. No. 4,284,722 claims a heat and acid stable alpha-amylase derived from an organism of the species *Bacillus stearothermophilus*.

Pace et al report in the Journal of Biological Chemistry that the thermal and guanidine hydrochloride denaturation of lysozyme has been investigated at various concentrations of tri-N-acetylglucosamine, which binds specifically at the active site of native lysozyme and that its presence leads to a readily observable stabilization of the protein to thermal and guanidine hydrochloride denaturation.

Chloride ion has been added to aqueous solutions of alpha-amylase which has been found to provide some thermal stabilization although the primary purpose for such addition is pH adjustment.

In U.S. Pat. No. 4,497,897 there is disclosed a method for enhancing the shelf life during storage of protease from Subtilisin Carlsberg which involves the addition of calcium ion and a water soluble carboxylate selected from the group of formate, acetate, propionate and mixtures thereof to a solution of the enzyme.

U.S. Pat. No. 4,318,818 discloses a stabilized aqueous enzyme composition comprising:
- (a) from 0 to about 75% of a detergent surfactant;
- (b) from about 0.025% to about 10% of pure enzyme, preferably a proteolytic enzyme;
- (c) from 0% to about 60% of a low molecular weight primary or secondary alcohol;
- (d) from about 0.1% to about 10% of a short chain length carboxylic acid salt, preferably a formate;
- (e) a soluble calcium salt in sufficient quantity to provide 0.1 to 10 millimoles of calcium ion per liter; and
- (f) the balance being water.

In typical commercial operations, starch is liquefied using thermostable alpha-amylase at a temperature ranging from 80° C. to about 110° C. and at a pH above 6.0. Calcium salts (50-150 ppm $Ca^{++}$) are generally added for additional stabilization of the enzyme at the elevated temperatures. These conditions for the enzymatic liquefaction of starch have three disadvantages. First, the hydrolysis of starch above pH 6.0 and at a temperature of 80° C. or above promotes the isomerization of reducing groups of the starch resulting in the formation of maltulose upon subsequent conversion processes which causes a decrease in the final glucose yield. Secondly, the pH optimum of glucoamylase used in the subsequent saccharification of the liquefied starch to produce glucose for subsequent conversion to fructose is generally about 4.5 for Aspergillus type glucoamylases and about 5.0 in the case of Rhizopus type enzymes. Thus, when the starch is liquefied at a pH of 6.0 or above, the pH must be reduced before saccharification using glucoamylase is carried out. This pH adjustment increases the salt content of the resulting glucose syrup due to the addition of acid and consequently increases the expense for ion exchange resins which are required for removal of the excess salt. For the liquefaction to be carried out at a pH of 6.0 or less, additional calcium ion (up to about 500 ppm) must be added. This complicates the complete removal of any added calcium ion from the glucose syrup produced by saccharification of the starch when it is to be used in the production of high fructose corn syrup using glucose isomerase.

It would be desirable, and it is an object of the present invention, to provide a novel method for enhancing the thermal stability of alpha-amylase in aqueous solution. A further object is to provide a stabilized alpha-amylase composition prepared by this method.

An additional object is to provide such a composition which does not require the presence of added calcium ion and can be used to liquefy starch at low levels of calcium (25-50 ppm).

Another object is to provide such a composition which can be used in the high temperature liquefaction of starch at a pH as low as 5.0.

SUMMARY OF THE INVENTION

The present invention is a method for enhancing the thermal stability of bacterial alpha-amylase. The method involves adding a stabilizing amount of an amphiphile to an aqueous solution of the alpha-amylase. Also included within the scope of the present invention is the alpha-amylase solution stabilized by this method and its use in the liquefaction of starch.

DESCRIPTION OF THE INVENTION

The alpha-amylase useful in the present invention is produced by cultivating a suitable microorganism in a nutrient growth medium to produce the extracellular enzyme. The amphiphile stabilizer can be added either before or after removal of biomass or concentration of the enzyme solution. However, in a typical run, the microbial cells are removed from the alpha-amylase containing medium by conventional means such as centrifugation with decantation and/or filtration. The filtrate is then concentrated using ultrafiltration and vacuum evaporation to provide an aqueous solution of the enzyme having the desired activity level. It is this solution which is preferably stabilized by the method of the present invention.

The increase in thermal stability of the alpha-amylase solution is accomplished by the addition of a stabilizing amount of an amphiphile thereto. By the term amphiphile we mean a molecule or ion having a polar (water soluble) head and a non-polar (water-insoluble) tail. In addition, an amphiphile must be large enough for each end to display its own solubility behavior. The general structural formula of an amphiphile is given below:

where X represents a polar or ionic group, e.g. $COO^-$, $NH_4+$, $OH$, $SO_4=$, $SO_3=$ or $CONH_2$ and R is a non-polar moiety. Thus, different classes of amphiphiles are contemplated as being useful in contributing to the thermal stability of alpha-amylase. Examples of useful amphiphiles are alcohols such ethyl alcohol, propyl alcohol, butyl alcohol, benzyl alcohol; amines such as benylamine, butylamine, ethylamine, hexylamine and amides such as butyramide, acetamide, phenylacetamide, benzamide. While it is not our intent to be bound by any particular theory of how the invention operates, it is believed that amphiphiles contribute to the thermal stability of alpha-amylase due to electrostatic and hydrophobic interactions therebetween. In a preferred embodiment, the ionic group of the amphiphile is carboxylate with the ionic moiety being represented by the formula:

where R is H or an aliphatic or aromatic group containing from 1 to 14 carbon atoms. More specifically, R can be methyl, ethyl, n- or isopropyl, n- or isobutyl, phenyl or substituted phenyl. The carboxylate containing amphiphile can be introduced to the aqueous solution of alpha-amylase in the form of the corresponding carboxylic acid, but, due to the increased solubility of acid salts, it is preferred that a salt, e.g. a sodium or calcium salt of the corresponding carboxylic acid be used.

The carboxylate ion, typically in the form of its sodium salt, is added to the aqueous solution of alpha-amylase in a stabilizing amount, i.e. that amount which will increase the enzyme's resistance to thermal inactivation to a significant degree. Analysis of commercially available alpha-amylase preparations has revealed that they may contain up to 0.02 g of acetate ion per million units of enzyme activity in terms of MWU determined as set out in Example I. The presence of acetate ion probably results from the addition of acetic acid for pH adjustment, and its presence in this low concentration is not sufficient to provide meaningful thermal stability to the alpha-amylase. Typically, the concentration of acetate should be at least about $2.89 \times 10^3$ mole of acetate per mole of alpha-amylase using a molecular weight of 58,000 daltons for the alpha-amylase for calculation purposes. This corresponds to 0.24 g of acetate per million units of enzyme activity. The minimum levels of other amphiphiles needed for effective stabilization of the enzyme will vary depending on the particular material being used but can readily be determined without undue experimentation.

When acetate is used as the stabilizing agent, preparation of the stabilized alpha-amylase formulation is typically accomplished by adding the sodium salt of the acetate ion to an aqueous concentrate of alpha-amylase solution to a final concentration of 10 g of sodium acetate to 100 ml of enzyme concentrate having 170,000-180,000 MWU/ml activity. In another embodiment, the amphiphile is added to the starch, either before or after the addition of the alpha-amylase, in an amount sufficient to provide an equivalent ratio of amphiphile to alpha-amylase.

The method of practicing the present invention is further illustrated by the following examples.

EXAMPLE I

An alpha-amylase sample was produced by cultivating a mutant strain of *Bacillus licheniformis* in a suitable nutrient growth medium. After the fermentation, the microbial cells were removed by conventional means leaving the extracellular enzyme in solution. The enzyme containing solution was then concentrated using ultrafiltration and vacuum evaporation to the desired activity level of 340,000-360,000 MWU/g (Modified Wohlgemuth Unit per gram).

The alpha-amylase activity was measured by determining the hydrolysis of soluble starch using blue value reduction of a starch-iodine complex. In a typical run, 5 milliliters of 2% soluble starch buffered at pH 5.4 and 4 ml of water are incubated with 1 ml of properly diluted enzyme in a water bath maintained at 40° C. At timed intervals (5-30 minutes from the addition of enzyme) 1 ml aliquots were drawn and injected into a tube containing 5 ml of dilute iodine solution and mixed by inversion. The developed color was then compared in a Hellige No. 600-DA daylight comparator illuminator from Hellige, Inc. to monitor the approach of the reaction endpoint and the enzyme activity monitored as Modified Wohlgemuth Units. One Modified Wohlgemuth Unit (MWU) is that activity which dextrinizes 1 ml of soluble starch to a defined blue value in thirty minutes under the conditions of the assay using the following equation:

$$MWU/g = \frac{100 \times 30}{T \times W}$$

where
- 100 milligrams starch in each incubation mixture
- 30 defined dextrinizing time in minutes
- T time in minutes required to reach end point
- W weight in grams of enzyme added to incubation mixture in one milliliter aliquot of enzyme dilution Sodium acetate ($CH_3COONa$) was added to an appropriately diluted (340,000 MWU/ml—1700 MWU/ml or 0.2 mg/ml protein) enzyme solution in varying amounts while maintaining the solution's pH at 5.8. The enzyme activity of each solution was determined as previously described. The enzyme solution was then heated to 90° C. for 10 minutes. Activity was again determined after heating to determine what effect, if any, the addition of sodium acetate had on the thermal stability of the alpha-amylase. The results of this experiment for varying levels of sodium acetate are set out in Table 1.

TABLE 1
Effect of Acetate Concentrations on the Thermal Stability of Alpha-Amylase

| g Na Acetate per Million Units of Enzyme Activity | Activity (MWU/ml) | | Percent Residual Activity |
|---|---|---|---|
| | Room Temp. | After Heating | |
| Control 0 | 1714 | 0 | 0 |
| 0.235 | 1578 | 231 | 12.7 |
| 0.47 | 1714 | 286 | 15.7 |
| 2.35 | 1714 | 837 | 46.0 |
| 4.70 | 1818 | 735 | 40.4 |
| 11.75 | 1818 | 522 | 28.7 |

From Table 1 it can be determined that the addition of acetate ion in the form of sodium acetate enhances the thermal stability of alpha-amylase. Furthermore, the observed stabilization increased with increasing concentrations of acetate up to a maximum at 2.35 g Na acetate per million units of enzyme activity at which concentration level the thermal stability began to drop off.

EXAMPLE II

Sodium salts of monocarboxylic acids such as sodium formate ($HCOONa$), sodium acetate ($CH_3COONa$), sodium propionate ($CH_3CH_2COONa$) and sodium butyrate ($CH_3CH_2CH_2COONa$) were added to an enzyme solution containing 40 mg/ml protein (alpha-amylase activity, 340,000 MWU/ml) to a final concentration of 1.22 M.

Figure 1:
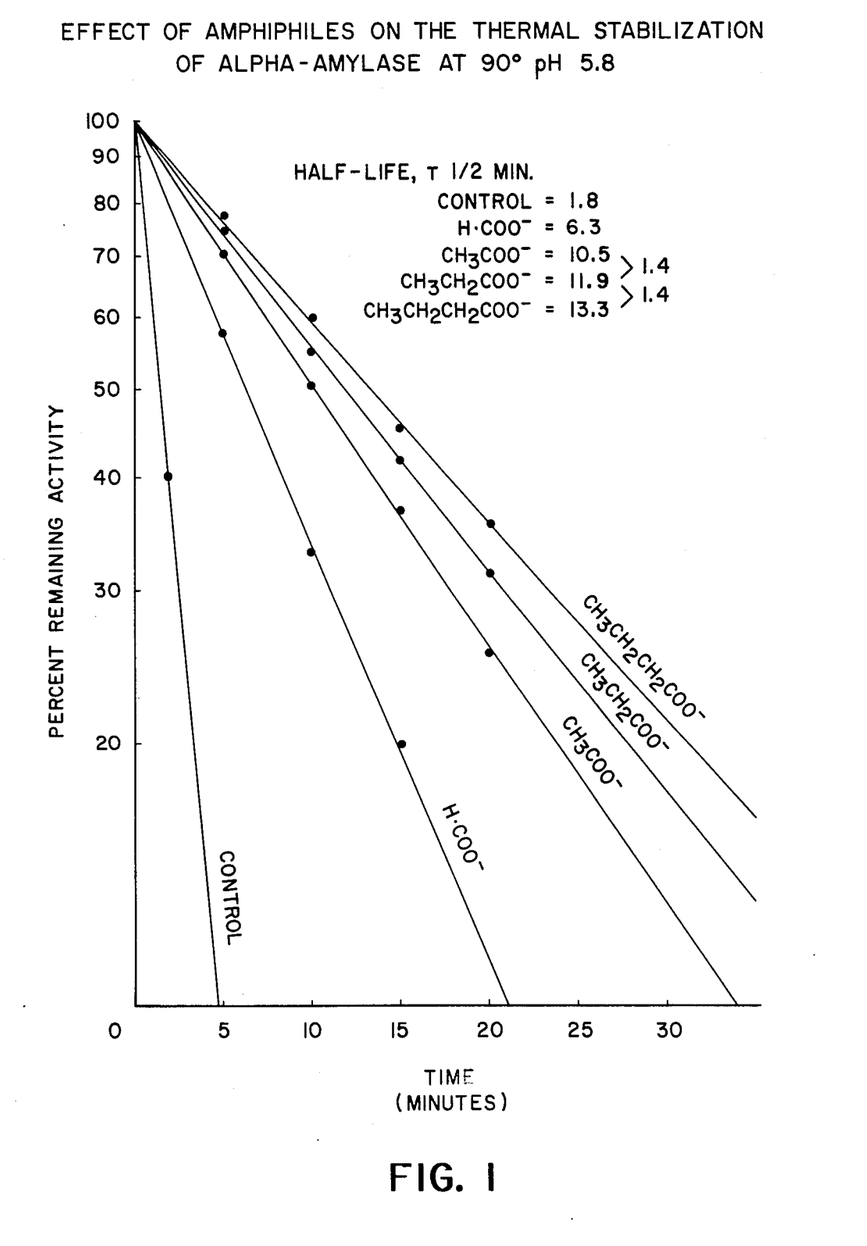

After proper dilution (1 × 100), the enzyme solutions, at pH 5.8, were heated to 95° C. and the heat stability of the enzyme was measured by determining the residual activity after heating the diluted enzyme for varying intervals of time. The time required to cause 50% inactivation (half-life $t_{\frac{1}{2}}$) was calculated from the plot of logarithm of the percent remaining activity against the incubation time. The results of these calculations are graphically presented in FIG. 1. From FIG. 1, the effect of increasing the aliphatic chain length on the thermal stabilization of alpha-amylase can be seen. Increasing the length of the aliphatic chain causes a proportional increase in the enhancement of thermal stability of the enzyme in aqueous solution at 95° C., pH 5.8. The thermal stabilization of the enzyme follows this order:

formate < acetate < propionate < butyrate.

The half-life of formate treated enzyme at 95° C., pH 5.8 was 6.3 minutes compared to 1.8 minutes for the control under identical conditions. However, introduction of a non-polar methyl group for hydrogen in formate caused a marked increase in the thermal stability of the enzyme (half-life = 10.5 minutes). Further increases in the length of the alkyl chain resulted in only a minimal increase in the half-life of the enzyme under the test conditions (1.4 minutes per $CH_2$ group). Thus, it can be seen that compounds containing a non-polar aliphatic chain (tail) and a polar carboxylate group (head) protect the enzyme from denaturation at high temperatures.

EXAMPLE III

In this experiment, organic acids containing non-polar aromatic groups were also tested. Sodium salts of benzoic acid ($C_6H_5COONa$), phenylacetic acid ($C_6H_5CH_2COONa$), phenylpropionic acid ($C_6H_5CH_2CH_2COONa$) and diphenylacetic acid ($C_{12}H_{10}CHCOONa$) were added to the enzyme solution (40 mg/ml protein alpha-amylase activity, 340,000 MWU/ml) to a final concentration of 1.22 M. These aromatic acids also resulted in a marked enhancement of the thermal stability of the alpha-amylase at 95° C., pH 5.8. The results of these experiments are summarized in Table 2 from which it can be determined that benzoic acid provided the least amount of stabilization among aromatic carboxylic acids tested while the diphenylacetate anion provided the most.

TABLE 2
Effect of Carboxylic Acid Salts Containing Non-Polar Aromatic Group on the Thermal Stabilization of Alpha-Amylase at 95° C., pH 5.8

| Sodium Salts | Structural Formula | Half-Life 95° C., pH 5.8 |
|---|---|---|
| Control | — | 1.8 minutes |
| Benzoic acid | C6H5—COO⁻ | 6 minutes |
| Phenylacetic acid | C6H5—CH2—COO⁻ | 7 minutes |
| Phenyl propionic acid | C6H5—CH2CH2COO⁻ | 12 minutes |
| Diphenylacetic | (C6H5)2CH—COO⁻ | 15 minutes |

EXAMPLE IV

Sodium acetate was added to the alpha-amylase concentrate containing 40 mg/ml (alpha-amylase activity, 340,000 MWU/ml) protein to a final concentration of 1.22 M (10% w/v). Then the pH of the aqueous enzyme solution was adjusted to 5.0, 5.6, 6.0, 7.0, 8.0 and 9.0 using sodium hydroxide. After 30 minutes, the enzyme was further diluted (1×100 fold) and heated to 95° C. for varying intervals of time and the remaining enzyme activity determined. At pH 5.0 and 5.5, the thermostability was measured at 85° C. For comparison, the effect of pH on the thermal stabilization of the enzyme in the absence of sodium acetate was also determined. The results of this experimentation are set out in Table 3.

TABLE 3
Effect of pH on the Thermal Stabilization of Alpha-Amylase

| Temp. | pH of the Treatment | Half-Life, t ½ Control | +0.0122 M Sodium Acetate |
|---|---|---|---|
| 85° C. | pH 5.0 | 1–1.5 minutes | 3 minutes |
|  | pH 5.5 | 6 minutes | 25 minutes |
| 95° C. | pH 6 | 3 minutes | 12 minutes |
|  | pH 7 | 6 minutes | 19 minutes |
|  | pH 8 | 11 minutes | 30 minutes |
|  | pH 9 | 15 minutes | 23 minutes |

The outstanding features that originated from the above results indicate the following:

(1) treatment of alpha-amylase with amphiphiles containing a carboxylic group and an aliphatic or aromatic non-polar residue causes a marked increase in the thermal stability of the enzyme;

(2) increasing the chain length of the non-polar group increases the thermal stability;

(3) aromatic residues have a greater effect than aliphatic residues.

While the patentability of this invention is not based on any particular mechanism, it is evident from the experimental evidence presented that the essential structure needed for the observed stabilizing effect consists of a polar head which interacts with polar functional groups of the enzyme and a non-polar hydrocarbon tail (aliphatic or aromatic) which interacts with the neighboring hydrophobic residues of the enzyme molecule. It may also be the case that the hydrocarbon tail shields a certain region of the enzyme molecule from surrounding water molecules. This offers a rigidity to the enzyme molecule required for structural resistance to thermal denaturation. It was observed that formate ion (HCOO−) was far less effective than the anions provided by acetic, propionic or butyric acids. The interaction of the hydrogen in the formate anion with bulk water tends to weaken the interaction between enzyme and anion whereas the methyl group in acetate can interact with neighboring hydrophobic side chains of the protein offering a marked increase in the thermal stabilization energy. Benzoic acid was least effective among the aromatic acid anions tested. It is possible that the double bond nature of the bond between the carboxyl group and the benzene ring may limit the flexibility of the carboxylate ion to interact with the polar residues of the enzyme molecule. The additional stabilization free energy responsible for increasing the thermostability of the alpha-amylase by added carboxylic acid salts was calculated and given in Table 4.

TABLE 4
Effect of Carboxylic Acids Containing Non-Polar Aliphatic and Aromatic Residues on the Thermal Stabilization of Alpha-Amylase at 95° C., pH 5.8

| Compound | t ½ (minutes) | $t_½/t_½°$ (F)[a] | $(-\Delta G°)$[b] (K cal/mole) |
|---|---|---|---|
| — | 1.8 | 1 | 0 |
| HCOONa | 6.3 | 3.5 | 0.9 |
| CH$_3$COONa | 10.5 | 5.8 | 1.3 |
| CH$_3$CH$_2$COONa | 11.9 | 6.6 | 1.4 |
| CH$_3$CH$_2$CH$_2$COONa | 13.3 | 7.4 | 1.5 |
| C$_6$H$_5$—COONa | 6.0 | 3.3 | 0.9 |
| C$_6$H$_5$—CH$_2$COONa | 7.0 | 3.9 | 1.0 |
| C$_6$H$_5$—CH$_2$CH$_2$COONa | 12.0 | 6.7 | 1.4 |
| C$_6$H$_5$—CH(C$_6$H$_5$)COONa | 15.0 | 8.3 | 1.5 |

[a] = Relative stabilization by the added ligand
[b] = The stabilization free energy is given by - R T ln F where T = 368K
F = relative stabilization factor
R = gas constant, 1.987 Cal/mole/degree
t ½° = half-life in the absence of ligand From Table 4, it can be determined that the addition of carboxylic acid salts to alpha-amylase increases the half-life of this enzyme. The relative stabilization factor, given as the ratio of t ½ in the presence of added compound to that in its absence (t ½°), increases with increasing chain length of carboxylic acid. This relative stabilization factor can be translated into additional stabilization free energy by using the relationship $\Delta G° = -RT \ln F$: where T is the temperature (°K.) to which the enzyme is heated, R is the gas constant and F is the relative stabilization factor. Formate confers a free energy of stabilization of 0.9 K Cal/mol. This is believed to arise primarily through an electrostatic interaction with a positively charged group of the enzyme, the effect being mainly entropic, contributed by the release of water molecule interactions with the charged groups. The additional stabilization by about 0.6 K Cal/mol. attributed to the butyl group (in butyrate) could result from a reinforcing hydrophobic interaction which also has a predominant entropic contribution to the free energy. The chainlength effects are incremented and the aromatic rings may be more than silent partners in the interaction in the sense that they could steer the interacting molecules towards optimal interaction sites. In any case, the interactions (although weak) appear to be specific with an electrostatic and a hydrophobic component. It is a cooperative interaction that confers a greater stabilization than could be afforded by the individual interactions. The indications are that the effective molecules interact with the enzymes in an interval region, not necessarily the active site, but all the same to help pressure the enzyme's conformation to remain intact for a longer time at the same temperature or sustain exposure at a higher temperature. Although surface interactions are not ruled out, the reinforcing effect of the pendant non-polar groups indicate an internalization of the interaction.

EXAMPLE V

The alpha-amylase stabilized by the method of the present invention is particularly suited to the liquefaction and conversion of starch in the production of malto-dextrins and subsequent production of glucose using glucoamylase. The high temperature jet cooking process to liquify starch using thermostable alpha-amylase described in U.S. Pat. No. 3,654,081 was used in this example. In a typical run, sixty pounds of corn starch was suspended in 33 liters of water to provide a starch concentration of 35-37% DSB and the pH adjusted to 5.0 using acetic acid. Taka-Therm ® thermostable alpha-amylase formulated with 10% sodium acetate containing 170,000 MWU/ml (Taka-Therm L-170) activity was added at 0.05% dry solids basis (DSB). The starch slurry was then gelatinized in a pilot plant steam jet cooker at 140° C. for 15 seconds. The gelatinized starch was flashed directly into a temperature regulated vessel maintained at 95° C. After the addition of 0.10% DSB Taka-Therm L-170,000 (formulated with 10% sodium acetate) to provide a total concentration of 20,400 MWU per 100 grams of starch, the liquefaction was continued for 20 minutes and then cooled to 85° C. The starch was then maintained at 85° C. for an average of 120 minutes. The dextrose equivalent (DE) was followed using a standard titration method during the liquefaction period.

The above experiment was repeated using Taka-Therm L-170 at pH 6.5 (pH adjusted using sodium hydroxide) in the presence of 150 ppm added calcium and in the presence of 500 ppm calcium at pH 5.0. No starch retrogradation was noted in either case. The results are summarized in the following Table 5 in which the term "spin residue" refers to the unhydrolyzed starch recovered after centrifugation.

the starch was liquefied by following the low temperature jet cooking (105°-107° C. for 3-5 minutes) process described by Scot et al, in U.S. Pat. No. 3,912,590. In a typical run, 70 lbs. of corn starch was suspended in 59 liters of water and the pH adjusted to 5.0 using acetic acid. Taka-Therm L-170,000 MWU/ml formulated with 10% sodium acetate was added to a final concentration of 0.15% DSB (20,400 MWU/100 g starch). The starch slurry containing enzyme was passed through a steam jet cooker maintained at 105°-107° C. and was held at that temperature for 3-5 minutes. After gelantinization, the starch was flashed into a temperature regulated vessel maintained at 95° C. for continued liquefaction for 2 hours. In another experiment, the liquefaction of starch was carried out at pH 6.3-6.5 (pH adjusted using sodium hydroxide) in the presence of 50 ppm added calcium. The DE progression was then compared and is set out in Table 6.

TABLE 6

D.E. Progression During Liquefaction of Starch in Low Temperature Jet Cooking Process

| Liquefaction Time at 95° C. | Standard Process | | Modified Process | |
|---|---|---|---|---|
| | pH 6.3-6.5 D.E. | +50 ppm Ca++ Residue (%) | pH 5.0 D.E. | + No Added Calcium Residue (%) |
| 30 min. | 13.01 | 0.4 | 15.6 | 0.1 |
| 60 min. | 15.52 | 0.4 | 17.70 | 0.1 |
| 90 min. | 16.02 | 0.2 | 20.65 | 0.04 |
| 120 min. | 18.59 | 0.2 | 23.50 | 0.04 |

From the data presented in Tables 5 and 6, it can be determined that the acetate stabilized alpha-amylase was thermostable enough to liquefy the starch at pH 5.0 in the absence of added calcium.

EXAMPLE VII

Figure 2:
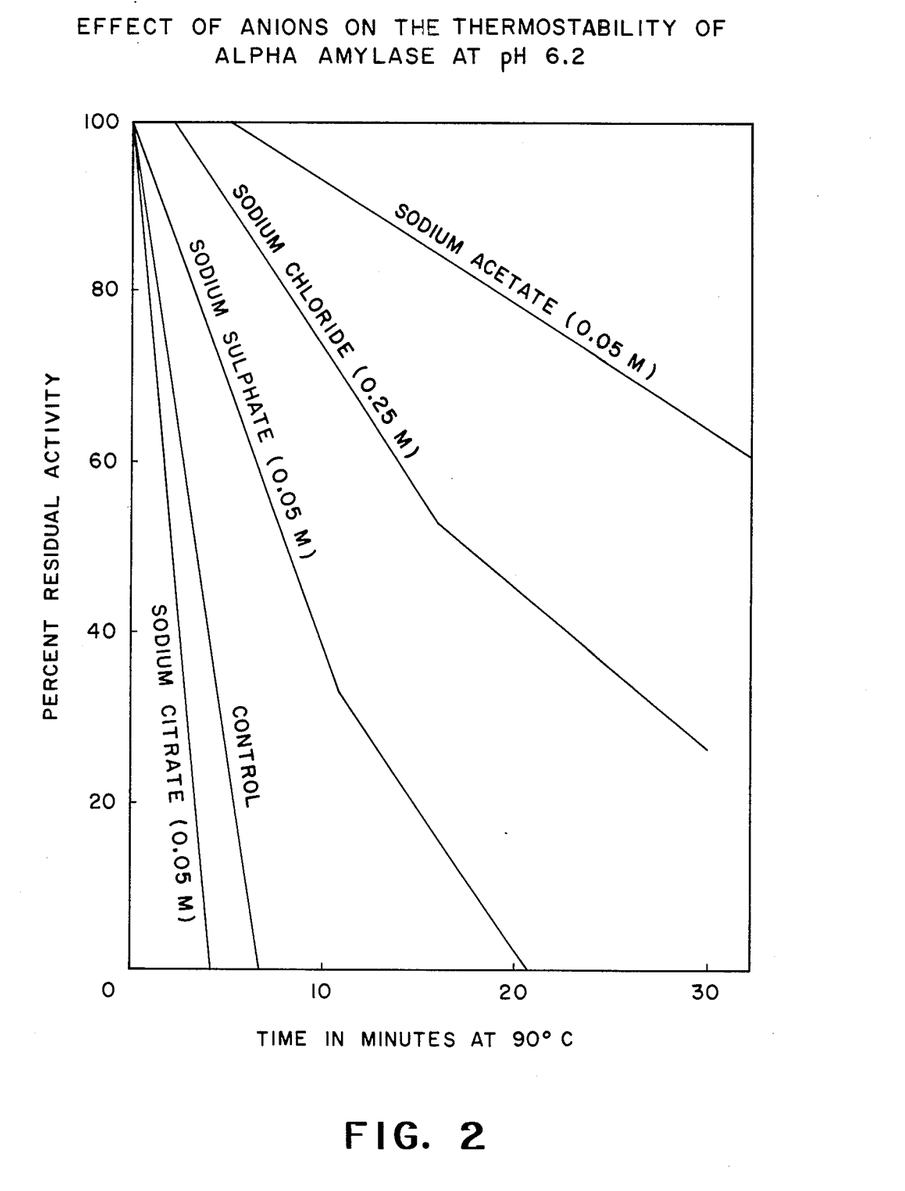

A comparative study was conducted in which the stability of alpha-amylase stabilized with acetate was compared with that containing anions known to have been added to commercially available alpha-amylase solutions. The activity of the various anion containing enzyme solutions was determined as previously described and the percent residual activity plotted as a function of time at 90° C. The results of this study are

TABLE 5

Dextrose Equivalent of the Liquefied Starch

| | Liquefaction pH | | | | | | | |
|---|---|---|---|---|---|---|---|---|
| | pH 6.3-6.5 | | | | pH 5.0 | | | |
| | Standard Process 150 ppm Ca++ | | Acetate Stab. Enzyme, No Ca++ | | Standard Process 500 ppm Ca++ | | Acetate Enzyme No Ca++ | |
| Sampling Time | DE | Spin Residue % | DE | Spin Residue % | DE | Spin Residue % | DE | Spin Residue % |
| After 20 min. at 95° C. | 5.47 | 2.5 | 4.59 | 1.6 | 4.5 | 3.0 | 8 | 2.5 |
| After 60 min. at 85° C. | 11.77 | 0.2 | 11.81 | 0.2 | 6.32 | 2.5 | 11 | 0.02 |
| After 120 min. at 85° C. | 20.17 | 0.02 | 21.89 | 0.02 | 8.30 | 0.08 | 15 | 0.02 |

The results summarized in Table 5 indicate that acetate stabilized alpha-amylase achieved a greater DE in the liquefied starch as compared to the use of alpha-amylase without added acetate. The addition of acetate not only replaces calcium during the enzymatic liquefaction of starch substrate but also enables one to liquefy the starch at a lower pH.

EXAMPLE VI

In addition to the high temperature jet cooking process (120°-140° C. for 15 seconds) for liquefying starch, graphically represented in FIG. 2. The stabilizing effects of the different anions against thermal inactivation of the enzyme followed this order: citrate<sulphate<chloride<acetate.

EXAMPLE VIII

Commercially, liquefied starch has a DE of around 10, so a series of liquefaction experiments were carried out to determine the optimum concentration of enzyme to produce a final DE of 10 in the liquefied starch.

Using this enzyme concentration, several liquefaction studies were carried out to evaluate the acetate stabilized Taka-Therm for commercial applicability in liquefying starch at low pH values under the low temperature jet cooking conditions described earlier. The results are summarized in Tables 7, 8 and 9.

of time to determine the effect of pH and high temperature on the chemical isomerization of the reducing groups. The liquefied starch was then saccharified using glucoamylase (100 DU/lb starch) at pH 4.2 and 60° C. for 48 hours. The carbohydrate profile of the final glucose syrup was determined by analyzing the sample

TABLE 7 pH 6.3–6.5
Taka-Therm L-170 at 0.08% DSB of Starch
(13,600 MWU/100 g Starch)
Concentration of Starch 32–33% DSB

| Study No. | Liquefaction Conditions | DE Progression and Spin Residues (5) | | | | | |
|---|---|---|---|---|---|---|---|
| | | Time (hr) | 0 | 0.5 | 1.0 | 1.5 | 2.0 |
| 1 | 50 ppm $Ca^{++}$ - Regular | DE | 6.32 | 7.91 | 9.37 | 10.97 | 11.59 |
| | TakaTherm L-170 | Spin Residue | 6.0 | 0.8 | 0.2 | 0.1 | 0.1 |
| 2 | 50 ppm $Ca^{++}$ - Acetate (10%) | DE | 8.91 | 10.51 | 11.54 | 12.76 | 13.91 |
| | Stabilized TakaTherm L-170 | Spin Residue | 6.0 | 0.15 | 0.15 | 0.15 | 0.15 |
| 3 | No $Ca^{++}$ - Acetate (10%) | DE | 6.71 | 8.53 | 10.05 | 11.51 | 12.89 |
| | Stabilized TakaTherm L-170 | Spin Residue | 4.0 | 0.40 | 0.1 | 0.1 | 0.1 |
| 4 | 50 PPM $Ca^{++}$ - Acetate (5%) | DE | 2.16 | 5.0 | 7.23 | 9.4 | 11.84 |
| | Stabilized TakaTherm L-170 | Spin Residue | 4.0 | 0.4 | 0.4 | 0.4 | 0.4 |
| 5 | No $Ca^{++}$ - Acetate (5%) | DE | 2.53 | 5.11 | 7.58 | 9.59 | 11.71 |
| | Stabilized TakaTherm L-170 | Spin Residue | 8.0 | 0.08 | 0.04 | 0.02 | 0.02 |

TABLE 8 pH of the Liquefaction = 5.5
Taka-Therm L-170 at 0.08% DSB (13,600 MWU/100 g Starch)
Starch Concentration 32–33% DSB

| Study No. | Liquefaction Conditions | DE Progression and Spin Residue (%) | | | | | |
|---|---|---|---|---|---|---|---|
| | | Time (hr) | 0 | 0.5 | 1.0 | 1.5 | 2.0 |
| 6 | 50 ppm $Ca^{++}$ - Regular | DE | ND | 2.72 | 3.96 | 4.57 | 5.5 |
| | TakaTherm L-170 | Spin Residue | ND | 0.3 | 0.4 | 0.4 | 0.4 |
| 7 | No $Ca^{++}$ - Acetate (10%) | DE | 2.39 | 5.77 | 6.47 | 9.89 | 11.58 |
| | Stabilized TakaTherm L-170 | Spin Residue | 2.0 | 0.15 | 0.1 | 0.1 | 0.1 |
| 8 | 50 ppm $Ca^{++}$ - Acetate (10%) | DE | 2.32 | 4.70 | 7.9 | 9.12 | 12.24 |
| | Stabilized TakaTherm L-170 | Spin Residue | 2.0 | 0.10 | 0.1 | 0.1 | 0.1 |
| 9 | 50 ppm $Ca^{++}$ - Acetate (5%) | DE | 1.53 | 4.58 | 7.37 | 9.37 | 10.74 |
| | Stabilized TakaTherm L-170 | Spin Residue | 1.0 | 0.08 | 0.06 | 0.04 | 0.04 |

TABLE 9 pH of the Liquefaction = 5.0
Taka-Therm L-170 at 0.08% DSB (13,600 MWU/100 g Starch)
Starch Concentration 32–33% DSB

| Study No. | Liquefaction Conditions | DE Progression and Spin residue (%) | | | | | |
|---|---|---|---|---|---|---|---|
| | | Time (hr) | 0 | 0.5 | 1.0 | 1.5 | 2.0 |
| 10 | 50 ppm $Ca^{++}$ - Regular | DE | 1.61 | 2.97 | 4.12 | 5.40 | 5.98 |
| | TakaTherm | Spin residue | 8.0 | 0.2 | 0.2 | 0.1 | 0.1 |
| 11 | No $Ca^{++}$ - Acetate (10%) | DE | 1.29 | 3.06 | 4.57 | 5.5 | 6.51 |
| | Stabilities TakaTherm L-170 | Spin residue | 4.0 | 0.2 | 0.1 | 0.1 | 0.1 |
| 12 | 50 ppm $Ca^{++}$ - Acetate (10%) | DE | 2.29 | 4.06 | 5.52 | 6.96 | 8.55 |
| | Stabilized TakaTherm L-170 | Spin residue | 1.0 | 0.04 | 0.04 | 0.04 | 0.04 |

The term "No $Ca^{++}$" in Tables 5, 7, 8 and 9 is intended to mean no added $Ca^{++}$ since the starch slurry and added water provided about 25–50 ppm calcium ion.

EXAMPLE IX

Effect of pH During Starch Liquefaction on the Formation of Maltulose

The liquefaction of starch under studies 1, 7 and 11 of Tables 7, 8 and 9 was carried out for an extended period using gas liquid chromatography and high pressure liquid chromatography techniques. Maltulose was separated from other disaccharides (maltose and isomaltose) by HPLC using an HPX-87 ion exchange column. The data so generated are summarized in the following Table 10.

TABLE 10

Effect of Liquefaction pH on the Formation of Maltulose

| Liquefaction Conditions | | Carbohydrate Profile (%) of the Glucose Syrup | | | | | |
|---|---|---|---|---|---|---|---|
| PH of the liquefaction | Time and Temp. | Glucose | Maltose | Maltulose | Isomaltose | Trisaccharide > $G_3$ | |
| pH 6.3–6.5 | 2 hr at 95° C. | 94.44 | 2.11 | Trace | 1.49 | 0.64 | 1.32 |
| | 4 hr at 95° C. | 93.62 | 2.08 | 0.81 | 1.07 | 0.81 | 3.60 |
| pH 5.5 | 2 hr at 95° C. | 94.32 | 1.9 | 0 | 1.39 | 0.87 | 1.52 |
| | 4 hr at 95° C. | 94.01 | 2.02 | 0 | 1.05 | 0.78 | 2.14 |

TABLE 10-continued

| Liquefaction Conditions | | Effect of Liquefaction pH on the Formation of Maltulose Carbohydrate Profile (%) of the Glucose Syrup | | | | | |
|---|---|---|---|---|---|---|---|
| PH of the liquefaction | Time and Temp. | Glucose | Maltose | Maltulose | Isomaltose | Trisaccharide | > G$_3$ |
| PH 5.0 | 2 hr at 95° C. | 95.18 | 1.69 | 0 | 1.36 | 0.45 | 1.33 |
|  | 4 hr at 95° C. | 95.04 | 1.74 | 0 | 1.37 | 0.55 | 1.31 |

From the above Table, it can be determined that the isomerization of the reducing group of the polysaccharide occurs above pH 6.0. Thus, elimination of maltulose formation during liquefaction of starch by controlling the pH during the liquefaction (pH below 6.0) results in an overall increase in the final glucose yield of greater than 1%.

EXAMPLE X

The following experiment was carried out to determine the effect of amphiphiles added directly to the starch slurry on the thermal stability of alpha-amylase activity during the liquefaction of starch at an elevated temperature and a low pH. Anhydrous sodium acetate was added to an aqueous starch slurry (31% DSB) to a final concentration of 0.01 molar (65g/21 gallons containing 70 pounds of starch). Calcium chloride was added to a level of 25 ppm (as Ca$^{++}$) and the pH adjusted to 5.5 using 10% sodium hydroxide. Alpha-amylase (Taka-Therm L-170) was added (20,400 MWU/100 g starch) and the starch was liquefied by following the low temperature jet cooking process described in Example VI. This experiment was repeated using a starch slurry containing sodium acetate in an amount equivalent to that derived when Taka-Therm L-170 formulated with 10% sodium acetate was used, i.e. 0.7 mM (4.6 g/21 gallons containing 70 pounds of starch). For comparison, starch was also liquefied at pH 5.5 in the presence of 25 ppm Ca$^{++}$ using regular Taka-Therm L-170 and Taka-Therm L-170 formulated with 10% sodium acetate. The results of these experiments are summarized in the following Table 11.

TABLE 11

Liquefaction pH = 5.5
Enzyme Concentration = 20,400 MWU/100 g Starch
Calcium Concentration: 25 ppm (Ca$^{++}$)
Starch = 31% DSB

| Liquefaction Conditions | DE Progression Time (hr) | | | |
|---|---|---|---|---|
|  | ½ | 1 | 1½ | 2 |
| Control, no acetate but 25 ppm added Ca$^{++}$ | 3.12 | 5.42 | 7.72 | 8.75 |
| Starch slurry containing 0.01 M sodium acetate and 25 ppm of added Ca$^{++}$ | 5.53 | 8.64 | 10.82 | 13.01 |
| Starch slurry containing 0.7 mM of sodium acetate (4.6 g/21 gallon of starch slurry) + 25 ppm of added Ca$^{++}$ | 4.15 | 6.11 | 8.87 | 10.25 |
| Taka-Therm stabilized with 10% sodium acetate and 18% sodium chloride. Calcium was added to 25 ppm during liquefaction. | 4.86 | 7.25 | 9.64 | 12.35 |

The data in the above Table clearly demonstrate that the addition of amphiphiles either to starch slurry or to enzyme has the same effect on the stabilization of alpha-amylase activity during liquefaction of starch.

What is claimed is:

1. A method for enhancing the thermal stability of bacterial alpha-amylase which comprises adding an amphiphile to an aqueous solution of the alpha-amylase wherein the amphiphile is represented by the formula:

$$R-COO^-$$

where R is an aliphatic or aromatic group containing from 1 to 14 carbon atoms and is present in a concentration of at least 2.89 mole of carboxylate per mole of alpha-amylase with a molecular weight of 58,000 daltons for the alpha-amylase being used for calculation purposes and the aqueous solution contains no more than about 50 ppm calcium ion.

2. The method of claim 1 wherein the alpha-amylase is derived from an organism of the species *Bacillus subtilis, B. licheniformis, B. stearothermophilus* or *B. coagulans*.

3. The method of claim 2 wherein the organism is of the species *B. licheniformis*.

4. The method of claim 1 wherein R is methyl, ethyl, n-propyl or isopropyl, n-butyl or isobutyl, phenyl or substituted phenyl.

5. The method of claim 1 wherein the carboxylate containing amphiphile is added to the aqueous solution of alpha-amylase in the form of its alkali metal salt.

6. The method of claim 5 wherein the alkali metal is sodium.

7. The method of claim 1 wherein the amphiphile is acetate and it is added to the aqueous alpha-amylase solution to a concentration of at least 0.24 g of acetate ion per million units of enzyme activity expressed in terms of modified Wohlgemuth Units.

8. A stabilized concentrated aqueous solution of alpha-amylase which contains an amphiphile represented by the formula:

$$R-COO^-$$

where R is H or an aliphatic or aromatic group containing from 1 to 14 carbon atoms and is present in a concentration of at least 2.89 mole of carbohydrate per mole of alpha-amylase with a molecular weight of 58,000 daltons for the alpha-amylase being used for calculation purposes and wherein the aqueous solution contains no more than about 50 ppm calcium ion.

9. A method of stabilizing an aqueous solution of alpha-amylase produced during the growth in a suitable nutrient medium of a bacteria from the species of the species *Bacillus licheniformis* which method involves adding an alkali metal acetate to the solution in an amount sufficient to provide a concentration of acetate ion of at least 0.24 g of acetate ion per million units of alpha-amylase activity expressed in terms of Modified Wohlgemuth Units.

10. The method of claim 9 wherein the alpha-amylase is present in the solution in sufficient quantity to provide an activity of 170,000 to 180,000 Modified Wohlgemuth Units per ml.

11. The method of claim 9 wherein the alkali metal is sodium.

12. A stabilized aqueous solution of alpha-amylase produced by a bacteria from the species *Bacillus licheniformis* which contains acetate ion in an amount of at least 0.24 g of acetate ion per million units of alpha-amylase activity expressed in terms of Modified Wohlgemuth Units.

13. The solution of claim 12 which contains a sufficient quantity of alpha-amylase to provide an activity of 170,000 to 180,000 Modified Wohlgemuth Units per ml.

14. A method for converting starch to a starch hydrolysate which comprises contacting the starch with an aqueous solution of alpha-amylase in the presence of an amphiphile represented by the formula:

$$R-COO^-$$

where R is H or an aliphatic or aromatic group containing from 1 to 14 carbon atoms and is present in a concentration of at least 2.89 mole of carboxylate per mole of alpha-amylase with a molecular weight of 58,000 daltons for the alpha-amylase being used for calculation purposes and wherein the aqueous solution contains no more than 50 ppm calcium ion.

15. The method of claim 14 wherein the amphiphile is acetate ion and is present in the alpha-amylase solution in an amount of at least 0.24 g of acetate per million units of enzyme activity expressed in terms of Modified Wohlgemuth Units.

16. The method of claim 14 wherein the starch conversion is carried out at a pH of from about 5.0 to 6.0.

17. The method of claim 14 wherein the amphiphile is added to the aqueous solution of alpha-amylase.

18. The method of claim 14 wherein the amphiphile is added to the starch either before or after addition of the alpha-amylase.

19. A method for the liquefaction of starch which comprises contacting the starch with an aqueous solution of alpha-amylase produced by a bacteria of the species *Bacillus licheniformis* in the presence of acetate ion in an amount of at least 0.24 g of acetate per million units of enzyme activity expressed interms of Modified Wohlgemuth Units wherein the pH is maintained at a level of 5.0 to 6.0.

20. The method of claim 19 wherein the acetate ion is added to the aqueous solution of alpha-amylase.

21. The method of claim 19 wherein the amphiphile is added to the starch either before or after addition of the alpha-amylase.

* * * * *